US00PP27489P2

(12) United States Plant Patent
Atchison

(10) Patent No.: US PP27,489 P2
(45) Date of Patent: Dec. 20, 2016

(54) ***SCHEFFLERA* PLANT NAMED 'CAMILLE'**

(50) Latin Name: *Schefflera actinophylla*
Varietal Denomination: Camille

(71) Applicant: James K Atchison, Boynton Beach, FL (US)

(72) Inventor: James K Atchison, Boynton Beach, FL (US)

( * ) Notice: Subject to any disclaimer, the term of this patent is extended or adjusted under 35 U.S.C. 154(b) by 0 days.

(21) Appl. No.: 14/756,750

(22) Filed: Oct. 7, 2015

(51) Int. Cl.
*A01H 5/00* (2006.01)

(52) U.S. Cl.
USPC ..... Plt./377

(58) Field of Classification Search
USPC ..... Plt./377
See application file for complete search history.

*Primary Examiner* — Annette Para
(74) *Attorney, Agent, or Firm* — Penny J. Aguirre

(57) ABSTRACT

A new cultivar of *Schefflera actinophylla*, 'Camille' that is characterized by its dark green, very shiny foliage, its thick leaves, its very short leaf internode lengths, and its resistance to spider mites and bacterial leaf blight and leaf spot.

2 Drawing Sheets

Botanical classification: *Schefflera actinophylla.*
Variety denomination: 'Camille'.

BACKGROUND OF THE INVENTION

The present invention relates to a new and distinct cultivar of *Schefflera actinophylla* and will be referred to hereafter by its cultivar name, 'Camille'. 'Camille' is a new cultivar of umbrella plant grown for use as an ornamental tropical plant.

'Camille' was discovered by the Inventor as a naturally occurring branch mutation on an unnamed and unpatented plant of *Schefflera actinophylla* that was growing in a container at his nursery in Delray Beach, Fla. in April of 2005.

Asexual propagation of the new cultivar was first accomplished by air layering by the Inventor in Delray Beach, Fla. in 2005. Asexual propagation by air layering and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Camille' as a unique cultivar of *Schefflera.*

1. 'Camille' exhibits dark green, very shiny foliage.
2. 'Camille' exhibits thick leaves.
3. 'Camille' exhibits very short leaf internode lengths in comparison to the species.
4. 'Camille' exhibits resistance to spider mites and bacterial leaf blight and leaf spot.

The parent of 'Camille' differs from 'Camille' in having leaves that are thinner, light green in color, and less shiny, in having a faster growth rate, and in having longer leaf internode lengths. In Inventor is unaware of any other cultivars of *Schefflera actinophylla.*

BRIEF DESCRIPTION OF THE DRAWINGS

The accompanying colored photographs illustrate the overall appearance and distinct characteristics of the new cultivar. The photographs were taken of plants six months in age (from an air layer) as grown outdoors in a two-gallon container Delray Beach, Fla.

Figure 1:
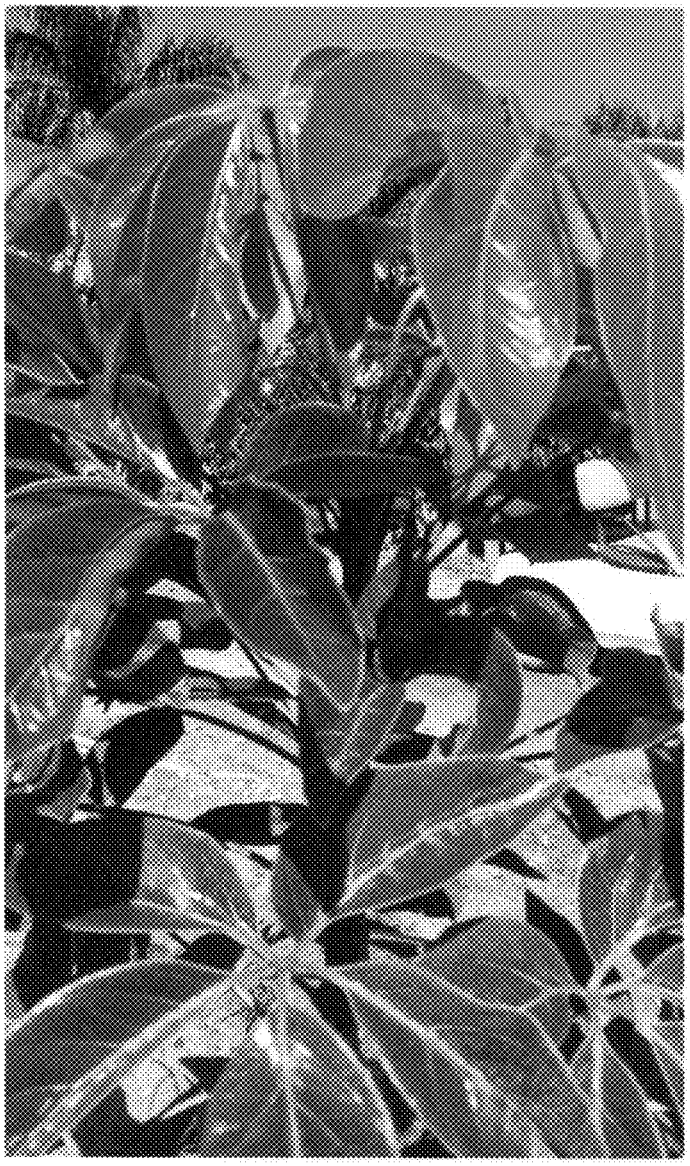
FIG. 1 provides a side view of a plant of 'Camille' and shows its short leaf internode lengths.
Figure 2:
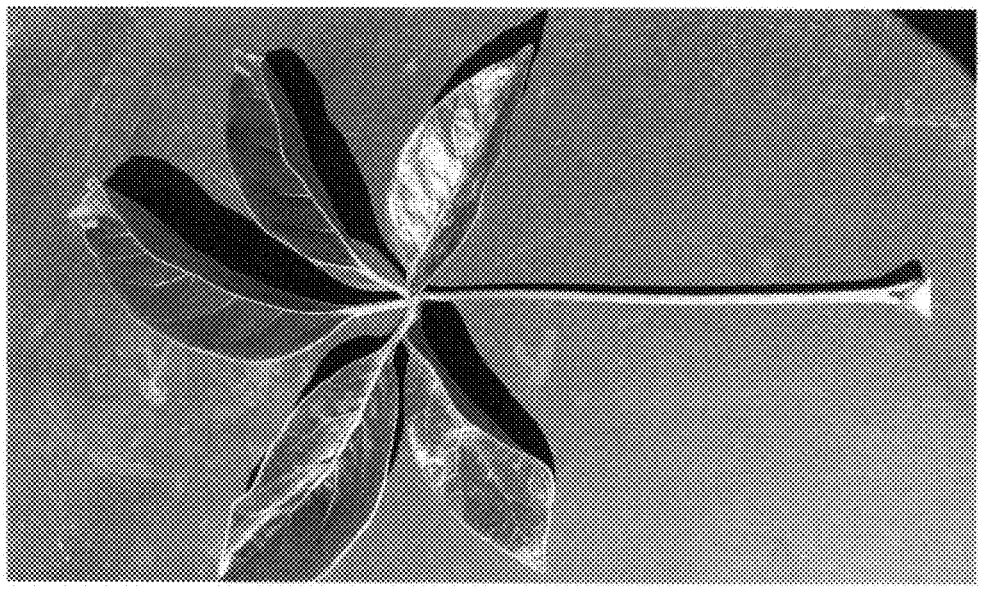
FIG. 2 provides a close-up view of a leaf of 'Camille'.
Figure 3:
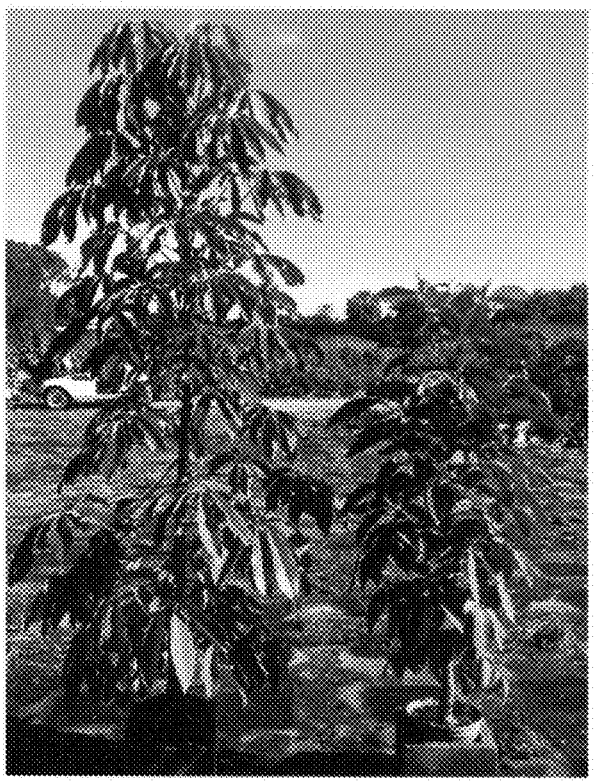
FIG. 3 provides a comparison between a plant of 'Camille' (right) and the parent plant, *Schefflera actinophylla* (left).

The colors in the photographs are as close as possible with the digital photography and printing techniques utilized and the color codes in the detailed botanical description accurately describe the *Schefflera.*

DETAILED BOTANICAL DESCRIPTION

The following is a detailed description of six month-old plants (from an air layer) as grown outdoors in 2-gallon containers in Delray Beach, Fla. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Plant type.*—Tropical.

*Plant habit.*—Upright with short leaf internode lengths.

*Height and spread.*—Reaches an average of 2.5 m in height and 0.9 to 1.2 m in spread when mature.

*Cold hardiness.*—Tropical, tolerant to temperatures down of 32° F.

*Diseases and pests.*—Has been observed to be resistance to spider mites (*Tetranychus urticae*) and bacterial leaf blight (caused by *Pseudomonas cichorii*) and leaf spot (caused by *Xanthomonas campestris* pv. *Hederae*).

*Propagation*—Air layering and stem cuttings.

*Growth rate.*—Vigorous by more moderate than the parent plant, approximately 6 months to produce plant 1.2 m in height in a 2-gallon container.

*Roots.*—Fibrous roots (199C in color) arise from stem sections near the soils line (same color as mature stem, and up to 1 cm in diameter).

Stem description:

*Stem size.*—1 m in length and 3.5 cm in diameter measured 15 cm above soil level.

*Stem color.*—Newer apical growth; a blend of 144A, 144B, and 144C, basal mature stem; a blend of 156A, 199A and 199B.

*Stem surface texture.*—Newer apical growth; smooth and glabrous very vertical lenticels; an average of 14 per stem area 2 cm in length and width, an average of 2 mm in length and 1 mm in width, 159A in color, basal mature stem; moderately rough bark with horizontal banding, lenticels are not visible.

*Stem aspect.*—Erect.

*Lateral branches.*—None.

*Internode length.*—An average of 1.3 cm.

Foliage description:

*Leaf shape.*—Ovate overall.

*Leaf division.*—Palmately compound (5 leaflets).

*Leaf fragrance.*—None.

*Leaf attachment.*—Long petiolate.

*Leaf orientation.*—Pendant from petiole.

*Leaf size.*—An average of 23 cm in length and 17 cm in width.

*Leaf quantity.*—An average of 33 per stem 1 m in length.

*Leaflet shape.*—Elliptic.

*Leaflet base.*—Cuneate to occasionally oblique.

*Leaflet apex.*—Acute to slightly acuminate.

*Leaflet venation.*—Pinnate, moderately conspicuous on upper surface when mature, color on upper surface new and mature leaves 144C, color on lower surface on new and mature leaflets; mid rib 144C, other veins match leaf color.

*Leaflet margins.*—Very slightly undulate.

*Leaflet arrangement.*—5, palmate.

*Leaflet attachment.*—Petiolules.

*Leaflet surface.*—Upper surface; very glossy, lower surface; satiny.

*Leaflet color.*—New leaves; upper surface 137A with a tinge of 144A, lower surface 147A with a tinge of 144A, mature leaves; upper surface N137A with a tinge of 144A, 147A with a tinge of 144A.

*Leaflet size* (*mature leaves*).—Terminal leaflet; an average of 15 cm in length and 8 cm in width, lateral leaflets; an average of 12 cm in length and 5.5 cm in width, basal leaflets; an average of 9.5 cm in length and 4.5 cm in width.

*Leaflet substance.*—Thick and leathery.

*Petioles.*—Round in shape, an average of 15 cm in length and 4 mm in width with expanded region at attachment (clasping) 1 cm in width and length, color; a blend of 197A and 144A on mature leaves, a blend of 197A and 152D on mature leaves, surface texture is glabrous with very fine vertical lines, stipules; emerge from top of clasping attachment, lanceolate in shape, 1 cm in length and 3 mm in width, glabrous surface, 147A and 147B in color.

*Petiolules.*—Shape is flattened on the upper surface and rounded on the lower surface, glabrous surface texture, 144C in color.

Inflorescence description (not a distinguishing factor): Plants have not been observed to bloom to date.

It is claimed:

1. A new and distinct cultivar of *Schefflera* tree named 'Camille' as herein illustrated and described.

* * * * *